(12) United States Patent
Haydon et al.

(10) Patent No.: US 8,492,414 B2
(45) Date of Patent: Jul. 23, 2013

(54) ANTIBACTERIAL AGENTS

(75) Inventors: David John Haydon, Yarnton (GB); Ian Collins, Yarnton (GB); Lloyd George Czaplewski, Yarnton (GB)

(73) Assignee: Biota Scientific Management Pty Ltd, Notting Hill, Victoria (AU)

( * ) Notice: Subject to any disclaimer, the term of this patent is extended or adjusted under 35 U.S.C. 154(b) by 456 days.

(21) Appl. No.: 12/678,767

(22) PCT Filed: Sep. 22, 2008

(86) PCT No.: PCT/GB2008/003200
§ 371 (c)(1),
(2), (4) Date: Jun. 7, 2010

(87) PCT Pub. No.: WO2009/037485
PCT Pub. Date: Mar. 26, 2009

(65) Prior Publication Data
US 2010/0273837 A1 Oct. 28, 2010

(30) Foreign Application Priority Data
Sep. 20, 2007 (GB) .................... 0718335.3

(51) Int. Cl.
*A61K 31/41* (2006.01)

(52) U.S. Cl.
USPC ........................................ 514/361

(58) Field of Classification Search
None
See application file for complete search history.

(56) References Cited

FOREIGN PATENT DOCUMENTS
| EP | 1500643 A | 1/2005 |
| WO | 2007107758 A | 9/2007 |
| WO | WO 2007/107758 * | 9/2007 |

OTHER PUBLICATIONS

Williams et al (Foye's Principles of Medicinal Chemistry, Fifth Edition, pp. 59-63, 2002).*
International Search Report for PCT/GB2008/003200 dated Dec. 9, 2008.

* cited by examiner

*Primary Examiner* — Craig Ricci
(74) *Attorney, Agent, or Firm* — Banner & Witcoff, Ltd.

(57) ABSTRACT

Compounds of formula (IA) or (IB) have antibacterial activity: wherein W is =CH— or =N—; Ri and R2 are independently selected from hydrogen, fluoro and chloro, provided that Ri and R2 are not each hydrogen when W is =CH—; n is 0 or 1; X is —O—, —S—, or —CH$_2$—; and Q is (i) a phenyl radical, a naphthyl radical, a monocyclic carbocyclic or heteroaryl radical having 3 to 6 ring atoms, or a bicyclic heteroaryl radical having 5 to 10 ring atoms, any of which radicals being optionally substituted; or (ii) an optionally substituted $C_1$-$C_6$ alkyl, $C_2$-$C_6$ alkenyl, or $C_2$-$C_6$ alkynyl radical, which may optionally be interrupted by —O—, —S—, —S(O)—, —S(O$_2$)—, —NH—, —N(CH$_3$)—, —N(CH$_2$CH$_3$)—, —C—K=Oh or —C(=O)—O—.

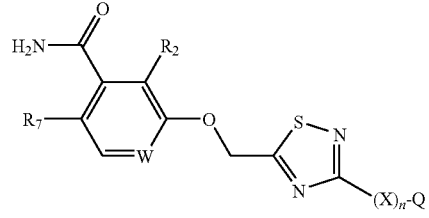

(IA)

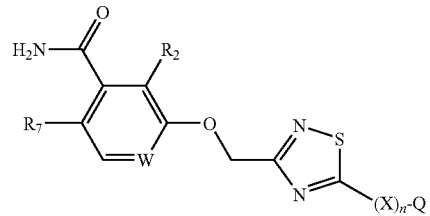

(IB)

9 Claims, No Drawings

ANTIBACTERIAL AGENTS

CROSS REFERENCE TO RELATED APPLICATIONS

This application is a National Stage application of co-pending PCT application PCT/GB2008/003200 filed Sep. 22, 2008, which claims the benefit of Great Britain application number 0718335.3 filed Sep. 20, 2007. These applications are incorporated herein by reference in their entireties.

This invention relates to a class of substituted benzamides and pyridylamides having antibacterial activity, the antibacterial use of members of that class, and to pharmaceutical compositions comprising such compounds.

BACKGROUND TO THE INVENTION

Many classes of antibacterial agents are known, including the penicillins and cephalosporins, tetracyclines, sulfonamides, monobactams, fluoroquinolones and quinolones, aminoglycosides, glycopeptides, macrolides, polymyxins, lincosamides, trimethoprim and chloramphenicol. The fundamental mechanisms of action of these antibacterial classes vary.

Bacterial resistance to many known antibacterials is a growing problem. Accordingly there is a continuing need in the art for alternative antibacterial agents, especially those that have mechanisms of action fundamentally different from the known classes.

Amongst the Gram-positive pathogens, such as staphylococci, streptococci, mycobacteria and enterococci, resistant strains have evolved/arisen which make them particularly difficult to eradicate. Examples of such strains are methicillin resistant *Staphylococcus aureus* (MRSA), methicillin-resistant coagulase negative staphylococci (MRCNS), penicillin resistant *Streptococcus pneumoniae* and multiply resistant *Enterococcus faecium*. In view of the rapid emergence of multidrug-resistant bacteria, the development of antibacterial agents with novel mechanisms of action that are effective against the growing number of resistant bacteria, particularly the vancomycin resistant enterococci and beta-lactam antibiotic-resistant bacteria, such as methicillin-resistant *Staphylococcus aureus*, is of utmost importance.

Cell division has been of considerable interest to the pharmaceutical industry as a target because it comprises a group of well conserved target proteins that are all essential for the viability of a wide range of bacteria, and their activities are completely different from those of the proteins involved in cell division of mammalian cells. A number of compounds that act on components of the cell division machinery have been described (Ohashi, Y. et al. J. Bacteriol. 181, 1348-1351 (1999), Jennings, L. D. et al. Bioorg. Med. Chem. 12, 5115-5131 (2004), Sutherland, A. G. et al. Org Biomol Chem 1, 4138-4140 (2003), Margalit, D. N. et al. Proc. Natl. Acad. Sci. USA 101, 11821-11826 (2004), Wang, J. et al. J. Biol. Chem. 278, 44424-44428 (2003), White, E. L. et al. J. Antimicrob. Chemother. 50, 111-114 (2002), Reynolds, R. C. et al. Bioorg. Med. Chem. Lett. 14, 3161-3164 (2004) and Stokes et al. J. Biol. Chem. 280, 39709-39715 (2005)). So far, most effort has been directed at the FtsZ protein, since it has several biochemical activities that can be assayed in vitro. Unfortunately, most of the compounds described so far either have relatively low potency, undesirable pharmacological properties or unknown specificity.

BRIEF DESCRIPTION OF THE INVENTION

Our co-pending International Patent Application No. PCT/GB2007/001012 is concerned with substituted benzamides or pyridylamides having antibacterial activity as evidenced by inhibition of bacterial growth by members of that class.

The present invention is concerned with antibacterial substituted benzamides and pyridylamides of the same class as that of PCT/GB2007/001012, but not specifically disclosed therein. The present compounds exhibit activity against strains of Gram-positive bacteria, such as staphylococci and bacilli, for example *Staphylococcus aureus*, *Staphylococcus epidermidis*, *Staphylococcus haemolyticus*, *Staphylococcus saprophyticus*, *Bacillus subtilis* and *Bacillus cereus*. Whilst the invention is not limited by any particular hypothesis as to the mechanism of action of the compounds, it is presently believed that such activity is mediated by the compounds inhibiting cell division through binding to FtsZ.

DETAILED DESCRIPTION OF THE INVENTION

According to the present invention there is provided a compound which is a substituted thiadiazolylmethoxybenzamide or thiadiazolylmethoxypyridylamide of formula (IA) or (IB), or a salt thereof:

wherein
W is =CH— or =N—;
$R_1$ and $R_2$ are independently selected from hydrogen, fluoro and chloro, provided that $R_1$ and $R_2$ are not each hydrogen when W is =CH—;
n is 0 or 1;
X is —O—, —S—, or —CH$_2$—;
Q is (i) a phenyl radical, a naphthyl radical, a monocyclic carbocyclic or heteroaryl radical having 3 to 6 ring atoms, or a bicyclic heteroaryl radical having 5 to 10 ring atoms, any of which radicals being optionally substituted; or (ii) an optionally substituted $C_1$-$C_6$ alkyl, $C_2$-$C_6$ alkenyl, or $C_2$-$C_6$ alkynyl radical, which may optionally be interrupted by —O—, —S—, —S(O)—, —S(O$_2$)—, —NH—, —N(CH$_3$)—, —N(CH$_2$CH$_3$)—, —C(=O)—, or —C(=O)—O—

In other broad aspects, the invention includes
(i) the use of a compound (IA) or (IB) as defined above in the manufacture of a composition for treating bacterial infection.
(ii) a method of treating bacterial infection in a subject suffering such infection comprising administering to the subject an amount of a compound (IA) or (IB) as defined above, sufficient to inhibit bacterial growth;
(iii) a method of treating bacterial contamination of a substrate comprising applying to the site of such contamination an amount of a compound (IA) or (IB) as defined above, sufficient to inhibit bacterial growth;

(iv) a compound (IA) or (IB) as defined above for use in a method of treatment of the human body;

(v) a compound (IA) or (IB) as defined above for use in treating bacterial infection;

(vi) an antibacterial composition comprising a compound of formula (IA) or (IB) as defined above, and a pharmaceutically acceptable carrier.

TERMINOLOGY

As used herein, the term "$(C_a$-$C_b)$alkyl" wherein a and b are integers refers to a straight or branched chain alkyl radical having from a to b carbon atoms. Thus when a is 1 and b is 6, for example, the term includes methyl, ethyl, n-propyl, iso-propyl, n-butyl, isobutyl, sec-butyl, t-butyl, n-pentyl and n-hexyl.

As used herein the term "$(C_a$-$C_b)$alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "$C_a$-$C_b$ alkynyl" wherein a and b are integers refers to straight chain or branched chain hydrocarbon groups having from a to b carbon atoms and having in addition at least one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the unqualified term "aryl" refers to a mono- or bi-cyclic carbocyclic aromatic radical. Illustrative of such radicals are phenyl and naphthyl.

As used herein the unqualified term "heteroaryl" refers to a mono-, or bi-cyclic aromatic radical containing one or more heteroatoms selected from S, N and O, and includes radicals having two such monocyclic rings, or one such monocyclic ring and one monocyclic aryl ring, which are fused or directly linked by a covalent bond. Illustrative of such radicals are thienyl, benzthienyl, furyl, benzfuryl, pyrrolyl, imidazolyl, benzimidazolyl, thiazolyl, benzthiazolyl, thiazolopyridinyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyridazinyl, triazinyl, indolyl and indazolyl.

Unless otherwise specified in the context in which it occurs, the term "substituted" as applied to any moiety herein means substituted with up to four compatible substituents, each of which independently may be, for example, $(C_1$-$C_6)$ alkyl, $(C_2$-$C_6)$alkenyl, $(C_2$-$C_6)$alkynyl, $(C_1$-$C_6)$alkoxy, hydroxy, hydroxy$(C_1$-$C_6)$alkyl, mercapto, mercapto$(C_1$-$C_6)$ alkyl, $(C_1$-$C_6)$alkylthio, halo (including fluoro, bromo and chloro), fully or partially fluorinated $(C_1$-$C_3)$alkyl, $(C_1$-$C_3)$ alkoxy or $(C_1$-$C_3)$alkylthio such as trifluoromethyl, trifluoromethoxy, and trifluoromethylthio, nitro, nitrile (—CN), oxo (=O), phenyl, phenoxy, monocyclic heteroaryl or heteroaryloxy with 5 or 6 ring atoms, —COOR$^A$, —COR$^A$, —OCOR$^A$, —SO$_2$R$^A$, —CONR$^A$R$^B$, —SO$_2$NR$^A$R$^B$, —NR$^A$R$^B$, OCONR$^A$R$^B$, —NR$^B$COR$^A$, —NR$^B$COOR$^A$, —NR$^B$SO$_2$OR$^A$ or —NR$^A$CONR$^A$R$^B$ wherein R$^A$ and R$^B$ are independently hydrogen or a $(C_1$-$C_6)$alkyl group or, in the case where R$^A$ and R$^B$ are linked to the same N atom, R$^A$ and R$^B$ taken together with that nitrogen may form a cyclic amino ring. Where the substituent is phenyl, phenoxy or monocyclic heteroaryl or heteroaryloxy with 5 or 6 ring atoms, the phenyl or heteroaryl ring thereof may itself be substituted by any of the above substituents except phenyl phenoxy, heteroaryl or heteroaryloxy. An "optional substituent" or "substituent" may be one of the foregoing specified groups.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids and the like. For a review on suitable salts, see *Handbook of Pharmaceutical Salts: Properties, Selection, and Use* by Stahl and Wermuth (Wiley-VCH, Weinheim, Germany, 2002).

It is expected that the compounds of the invention may be recovered in the form of hydrates or solvates. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water. References herein to compounds of formula (I) are to be understood as including such compounds in the form of hydrates or solvates thereof.

Compounds of the invention which contain one or more actual or potential chiral centres, because of the presence of asymmetric carbon atoms, can exist as a number of enantiomers or diastereoisomers with R or S stereochemistry at each chiral centre. The invention includes all such enantiomers and diastereoisomers and mixtures thereof.

Individual compounds of the invention may exist in several polymorphic forms and may be obtained in different crystal habits.

So-called 'prodrugs' of the compounds of formula (IA) and (IB) are also within the scope of the invention. Thus certain derivatives of the compounds which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and V. J. Stella) and *Bioreversible Carriers in Drug Design*, Pergamon Press, 1987 (ed. E. B. Roche, American Pharmaceutical Association; C. S. Larsen and J. Østergaard, Design and application of prodrugs, In Textbook of Drug Design and Discovery, $3^{rd}$ Edition, 2002, Taylor and Francis).

Prodrugs in accordance with the invention can, for example, be produced by replacing appropriate functionalities present in the compounds of formula (IA) and (IB) with certain moieties known to those skilled in the art as 'promoieties' as described, for example, in *Design of Prodrugs* by H. Bundgaard (Elsevier, 1985). Such examples could be a prodrug of a carboxyl group (such as —CO—O—CH$_2$—O—CO-tBu as used in the pivampicillin prodrug of ampicillin), an amide (—CO—NH—CH$_2$—NAlk$_2$) or an amidine (—C(=N—O—CH$_3$)—NH$_2$).

Also included within the scope of the invention are metabolites of compounds of formula (IA) and (IB), that is, compounds formed in vivo upon administration of the drug. Some examples of metabolites include
(i) where the compound of formula I contains a methyl group, an hydroxymethyl derivative thereof (—$CH_3$->—$CH_2OH$):
(ii) where the compound of formula I contains an alkoxy group, an hydroxy derivative thereof (—OR->—OH);
(iii) where the compound of formula I contains a tertiary amino group, a secondary amino derivative thereof (—$NR^1R^2$->—$NHR^1$ or —$NHR^2$);
(iv) where the compound of formula I contains a secondary amino group, a primary derivative thereof (—$NHR^1$->—$NH_2$);
(v) where the compound of formula I contains a phenyl moiety, a phenol derivative thereof (-Ph->-PhOH); and
(vi) where the compound of formula I contains an amide group, a carboxylic acid derivative thereof (—$CONH_2$->COOH).

Structural Aspects of Compounds of the Invention

In the compounds of the invention:

Of the two regioisomers (IA) and (IB), regioisomer (IA) is currently preferred;

W is =CH— or =N— but currently it is preferred that W be =CH—;

$R_1$ and $R_2$ are independently selected from hydrogen, fluoro and chloro, provided that $R_1$ and $R_2$ are not each hydrogen when W is =CH—; Currently it is preferred that $R_1$ and $R_2$ are independently fluoro or chloro, or one of $R_1$ and $R_2$ is hydrogen while the other is fluoro or chloro.

n is 0 or 1, and when n is 1 X is —O—, —S—, or —$CH_2$—;

Q is (i) a phenyl radical, a naphthyl radical, a monocyclic heteroaryl radical having 3 to 6 ring atoms, or a bicyclic heteroaryl radical having 5 to 10 ring atoms, any of which radicals being optionally substituted; or (ii) an optionally substituted $C_1$-$C_6$ alkyl, $C_2$-$C_6$ alkenyl, or $C_2$-$C_6$ alkynyl radical, which may optionally be interrupted by
—O—, —S—, —S(O)—, —S($O_2$)—, —NH—, —N($CH_3$)—, —N($CH_2CH_3$)—, —C(=O)—, or —C(=O)—O—;

In case (i), it is currently preferred that Q be optionally substituted pyridin-2-yl, or pyridin-3-yl, or especially optionally substituted phenyl. Also in case (i), it is currently preferred that any optional substituents in Q are selected from methyl, —$OCH_3$, —$OCH_2CH_3$, —$CF_3$, —$OCF_3$, ethyl, cyclopropyl, oxo, hydroxyl, —F, —Cl, —Br, cyano, acetyl, amino, methylamino, dimethylamino, acetylamino, carbamate, —$CONH_2$, nitro, —COOH and —$CH_2OH$. In case (i) n may be 0 or 1, but presently preferred is the case where n is 0.

Specific compounds of the invention include those selected from the group consisting of:

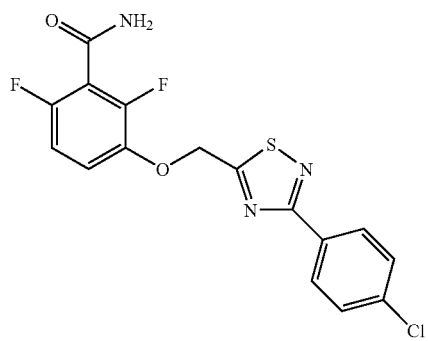

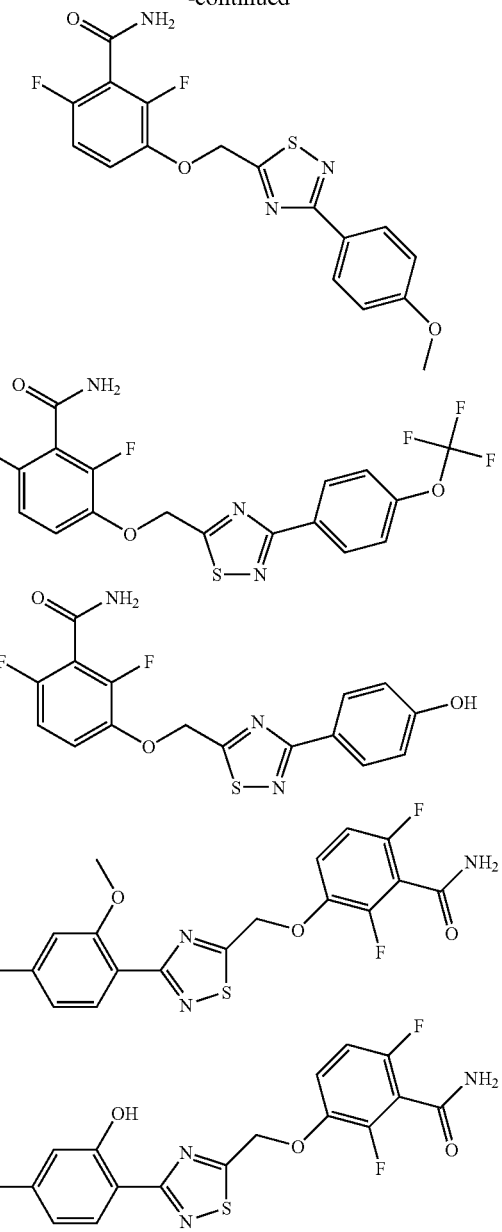

and salts, hydrates and solvates thereof.

Synthesis

There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to the one skilled in the art. Typical literature sources are "*Advanced Organic Chemistry*", 4<sup>th</sup> Edition (Wiley), J March, "*Comprehensive Organic Transformation*", 2<sup>nd</sup> Edition (Wiley), R. C. Larock, "*Handbook of Heterocyclic Chemistry*", 2<sup>nd</sup> Edition (Pergamon), A. R. Katritzky), review articles such as found in "*Synthesis*", "*Acc. Chem. Res.*", "*Chem. Rev*", or primary literature sources identified by standard literature searches online or from secondary sources such as "*Chemical Abstracts*" or "*Beilstein*".

Specifically, compounds (IA) may be prepared by the routes used for the preparation of the compounds of Examples 1-4 below or by analogous routes. Compounds (IB may be prepared by the general route summarised in Scheme A:

SCHEME A

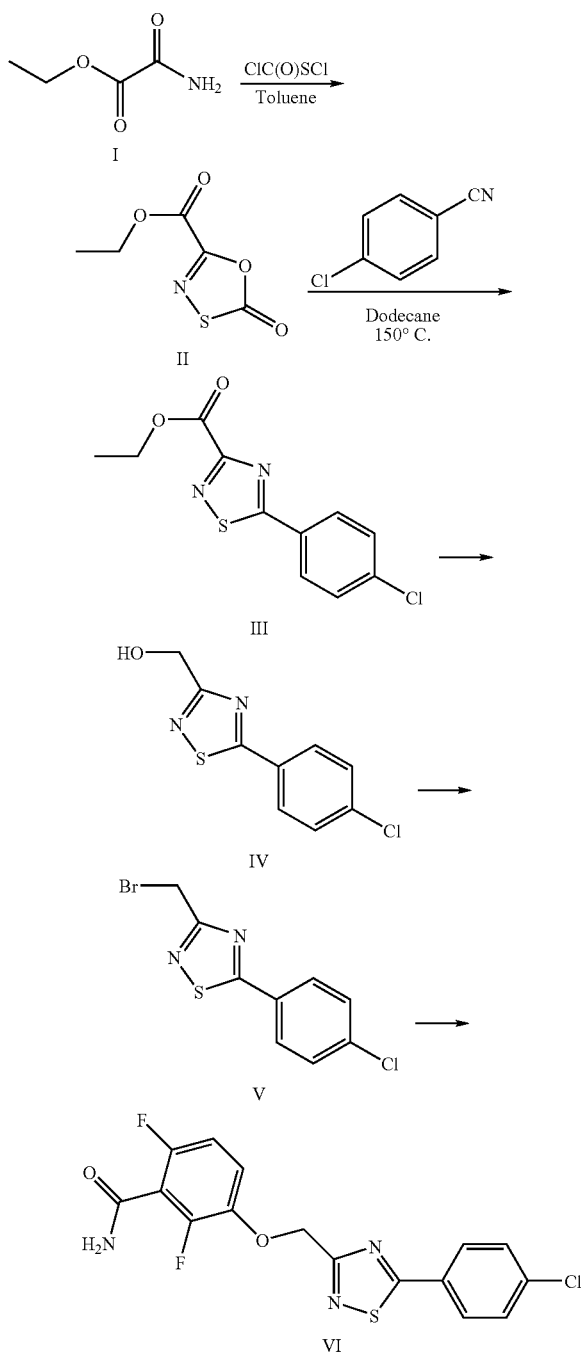

Ref: JOC; 42(10), 1977, 1813-1814.

Pharmaceutical Utilities

As mentioned above, the compounds with which the invention are concerned are antibacterially active, since they inhibit bacterial growth. They are therefore of use in the treatment of bacterial infection in humans and non-human animals e.g. other mammals, birds and fish. The compounds include those which inhibit growth of Gram-positive organisms such as *Bacillus subtilis* and *Staphylococcus aureus*.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy. As is required in the pharmaceutical art, safe and permitted doses will be determined by clinical trial, but daily dosages can vary within wide limits and will be adjusted to the individual requirements in each particular case. Typically, however, the dosage adopted for each route of administration when a compound is administered alone to adult humans is 0.0001 to 150 mg/kg body weight. Such a dosage may be given, for example, from 1 to 5 times daily. For intravenous injection a suitable daily dose is from 0.0001 to 150 mg/kg body weight. A daily dosage can be administered as a single dosage or according to a divided dose schedule.

The compounds with which the invention is concerned may be prepared for administration by any route consistent with their pharmacokinetic properties, such as oral, topical, or sterile parenteral solutions or suspensions. The orally administrable compositions may be in the form of tablets, capsules, powders, granules, lozenges, liquid or gel preparations. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium, either subcutaneously, or intravenously, or intramuscularly, or intrasternally, or by infusion techniques, in the form of sterile injectable aqueous or oleaginous suspensions. Depending on the vehicle and concentration used, the drug can either be suspended or dissolved in the vehicle. Advantageously, adjuvants such as a local anaesthetic, preservative and buffering agents can be dissolved in the vehicle.

The antibacterial compounds of the present invention may be administered in combination with other antibacterial agents, especially those having mechanisms of action different from those of the present compounds. Compounds having activities other than antibacterial may also be administered with the compounds of the invention, for example anti-inflammatory or antipyretic compounds.

Since the compounds with which the invention is concerned are antibacterially active and inhibit bacterial growth, they are also of use in treating bacterial contamination of a substrate, such as hospital instruments or work surfaces. In order to treat a contaminated substrate, the compounds may be applied to the site of such contamination in an amount sufficient to inhibit bacterial growth.

The following examples illustrate the synthesis of compounds with which the invention is concerned.

Scheme-1:

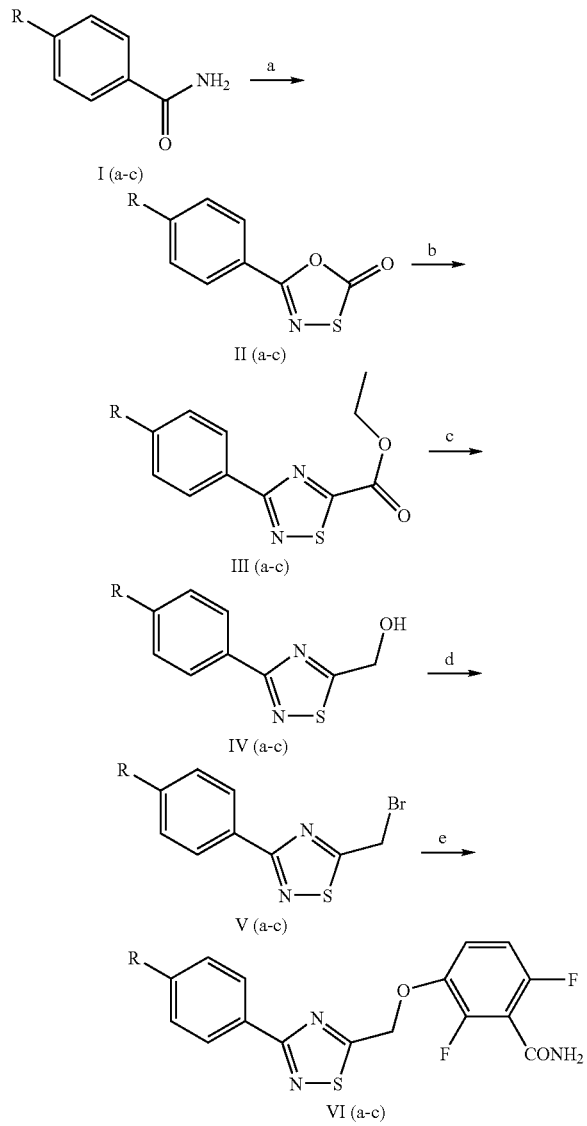

(a) Chlorocarbonylsulfenyl chloride, toluene, 80° C., 3 h; (b) Ethyl cyanoformate, n-dodecane, 150° C., 20 h; (c) NaBH$_4$, MeOH, 2 h; (d) PBr$_3$, toluene, 120° C., 5 min; (e) 2,6-Difluoro-3-hydroxybenzamide, K$_2$CO$_3$, DMF.

R =
a = Cl; b = OMe; c = OCF$_3$ 5-(4-Chlorophenyl)-[1,3,4]oxathiazol-2-one: (II-a)

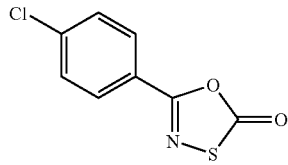 [SMILES: O=c1oc(-c2ccc(Cl)cc2)ns1]

To a solution of 4-chlorobenzamide (0.25 g, 1.60 mmol) in toluene (10 ml) was added chlorocarbonylsulfenyl chloride (0.70 ml, 8.03 mmol). The resulting reaction mixture was refluxed at 80° C. for 3 h. After the completion of the reaction (TLC monitoring), the mixture was concentrated, added diethyl ether and washed twice with water, twice with 5% NaHCO$_3$, again with water, and was dried (Na$_2$SO$_4$), concentrated under vacuum to give the product (crude yield 0.520 g) that was carried forward to the next step without further purification.

5-(4-Methoxyphenyl)-[1,3,4]oxathiazol-2-one: (II-b)

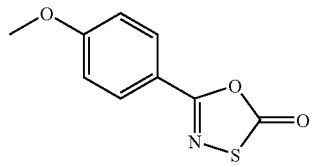

To a solution of 4-methoxybenzamide (0.30 g, 1.10 mmol) in toluene (10 ml) was added chlorocarbonylsulfenyl chloride (0.80 ml, 9.92 mmol). The resulting reaction mixture was refluxed at 80° C. for 3 h. After the completion of the reaction (TLC monitoring), the mixture was concentrated, added diethyl ether and washed with twice with water, twice with 5% NaHCO$_3$, again with water, and was dried (Na$_2$SO$_4$), concentrated under vacuum to give the product (crude yield 0.475 g) that was carried forward to the next step without further purification.

5-(4-Trifluoromethoxyphenyl)-[1,3,4]oxathiazol-2-one: (II-c)

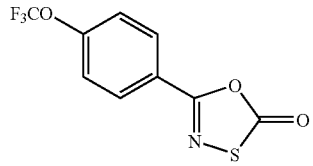 [SMILES: O=c1oc(-c2ccc(OC(F)(F)F)cc2)ns1]

To a solution of 4-trifluoromethoxybenzamide (0.50 g, 2.43 mmol) in toluene (10 ml) was added chlorocarbonylsulfenyl chloride (0.50 ml, 6.09 mmol). The resulting reaction mixture was refluxed at 90° C. for 2 h. After the completion of the reaction (TLC monitoring), the mixture was concentrated, added diethyl ether and washed twice with water, twice with 5% NaHCO$_3$, again with water, and was dried (Na$_2$SO$_4$), concentrated under vacuum to give the product (crude yield 0.74 g) that was carried forward to the next step without further purification. MS ES+ (264.18).

3-(4-Chlorophenyl)-[1,2,4]thiadiazole-5-carboxylic acid ethyl ester: (III-a)

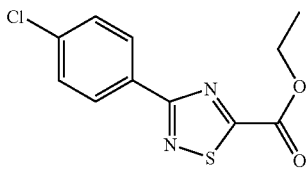 [SMILES: CCOC(=O)c1nc(-c2ccc(Cl)cc2)ns1]

To a solution of 5-(4-chlorophenyl)-[1,3,4]oxathiazol-2-one (0.60 g, 2.80 mmol) in n-dodecane (0.80 ml) was added ethyl cyanoformate (1.10 ml, 11.20 mmol). The resulting reaction mixture was refluxed for 20 h at 150° C. After the completion of the reaction (TLC monitoring), added ice-cold water and extracted with ethyl acetate (3×75 ml). The combined organic layer was dried over $Na_2SO_4$, filtered and concentrated under vacuum. The crude residue was purified over silica gel (100-200 M, 20% EtOAc—Hexane) to get the product (0.23 g, 30%).

3-(4-Methoxyphenyl)-[1,2,4]thiadiazole-5-carboxylic acid ethyl ester: (III-b)

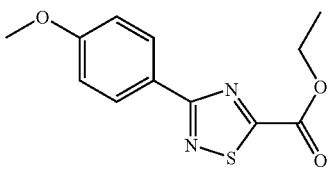 [SMILES: CCOC(=O)c1nc(-c2ccc(OC)cc2)ns1]

To a solution of 5-(4-methoxyphenyl)-[1,3,4]oxathiazol-2-one (0.47 g, 2.24 mmol) in n-dodecane (0.70 ml) was added ethyl cyanoformate (0.90 ml, 8.10 mmol). The resulting reaction mixture was refluxed for 20 h at 150° C. After the completion of the reaction (TLC monitoring), added ice-cold water and extracted with ethyl acetate (3×50 ml). The combined organic layer was dried over $Na_2SO_4$, filtered and concentrated under vacuum. The crude residue washed with ether to get the desired product (0.24 g, 40%). MS ES+ (265.08).

3-(4-Trifluoromethoxyphenyl)-[1,2,4]thiadiazole-5-carboxylic acid ethyl ester: (III-c)

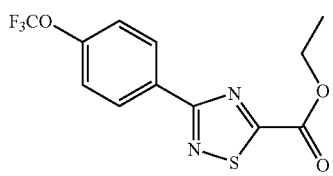 [SMILES: CCOC(=O)c1nc(-c2ccc(OC(F)(F)F)cc2)ns1]

To a solution of 5-(4-trifluoromethoxyphenyl)-[1,3,4]oxathiazol-2-one (0.74 g, 2.81 mmol) in n-dodecane (0.50 ml) was added ethyl cyanoformate (1.10 ml, 11.24 mmol). The resulting reaction mixture was refluxed for 24 h at 150° C. After the completion of the reaction (TLC monitoring), added ice-cold water and extracted with ethyl acetate (3×50 ml). The combined organic layer was dried over $Na_2SO_4$, filtered and concentrated under vacuum. The crude residue was purified over silica gel (100-200 M, 2% EtOAc-Hexane) to get the product (0.11 g, 12%).

[3-(4-Chlorophenyl)-[1,2,4]thiadiazol-5-yl]-methanol: (IV-a)

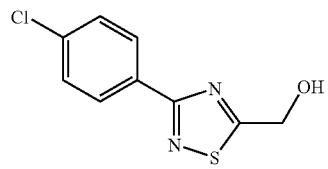 [SMILES: OCc1nc(-c2ccc(Cl)cc2)ns1]

To a solution of 3-(4-chlorophenyl)-[1,2,4]thiadiazole-5-carboxylic acid ethyl ester (0.20 g, 0.74 mmol) in MeOH (10 ml) was added sodium borohydride (0.048 g, 1.26 mmol) portion wise. The resulting reaction mixture was stirred at room temperature for 2 h. After the completion of the reaction (TLC monitoring), the reaction mass was cooled to 0° C., quenched it with 2 ml of water and concentrated under vacuum. Added water (50 ml) and extracted with ethyl acetate (3×50 ml). The combined organic layer was dried over $Na_2SO_4$, filtered and concentrated under vacuum to get the product (0.17 g) that was carried forward to the next step without further purification.

[3-(4-Methoxyphenyl)-[1,2,4]thiadiazol-5-yl]-methanol: (IV-b)

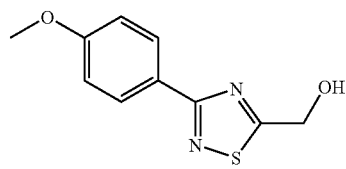

To a solution of 3-(4-methoxyphenyl)-[1,2,4]thiadiazole-5-carboxylic acid ethyl ester (0.24 g, 0.90 mmol) in MeOH (10 ml) was added sodium borohydride (0.058 g, 1.54 mmol) portion wise. The resulting reaction mixture was stirred at room temperature for 2 h. After the completion of the reaction (TLC monitoring), the reaction mass was cooled to 0° C., quenched it with 2 ml of water and concentrated under vacuum. Added water (50 ml) and extracted with ethyl acetate (3×50 ml). The combined organic layer was dried over $Na_2SO_4$, filtered and concentrated under vacuum. The crude residue was purified over silica gel (100-200 M, 20% EtOAc-Hexane) to get the product (0.072 g, 43%) that was carried forward to the next step without further purification.

¹H NMR (CDCl₃, 400 MHz): δ 3.87 (s, 3H), 5.16 (d, J=5.60 Hz, 2H), 6.99 (d, J=8.40 Hz, 2H) and 8.22 (d, J=8.40 Hz, 2H).

[3-(4-Trifluoromethoxyphenyl)-[1,2,4]thiadiazol-5-yl]-methanol: (IV-c)

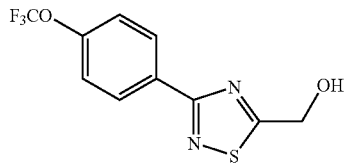 [SMILES: OCc1nc(-c2ccc(OC(F)(F)F)cc2)ns1]

To a solution of 3-(4-trifluoromethoxyphenyl)-[1,2,4]thiadiazole-5-carboxylic acid ethyl ester (0.11 g, 0.35 mmol) in MeOH (10 ml) was added sodium borohydride (0.022 g, 0.59 mmol) portion wise. The resulting reaction mixture was stirred at room temperature for 2 h. After the completion of the reaction (TLC monitoring), the reaction mass was cooled to 0° C., quenched it with 2 ml of water and concentrated under vacuum. Added water (50 ml) and extracted with ethyl acetate (3×50 ml). The combined organic layer was dried over Na₂SO₄, filtered and concentrated under vacuum to get the product (0.10 g) that was carried forward to the next step without further purification.

5-Bromomethyl-3-(4-chlorophenyl)-[1,2,4]thiadiazole: (V-a)

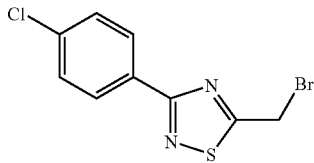 [SMILES: Clc1ccc(-c2nsc(CBr)n2)cc1]

To a solution of [3-(4-chlorophenyl)-[1,2,4]thiadiazol-5-yl]-methanol (0.18 g, 0.80 mmol) in toluene (10 ml) was added PBr₃ (0.11 ml, 1.19 mmol) and the resulting reaction mixture was refluxed at 120° C. for 15 min. After the completion of the reaction (TLC monitoring), the reaction mixture was cooled to 0° C., added water (50 ml) and extracted with ethyl acetate (3×50 ml). The combined organics was washed with saturated NaHCO₃ solution, dried over Na₂SO₄, filtered and concentrated under vacuum. The crude residue was purified over silica gel (100-200 M, 10% EtOAc-Hexane) to get the desired product (0.08 g, 35%).

5-Bromomethyl-3-(4-methoxyphenyl)-[1,2,4]thiadiazole: (V-b)

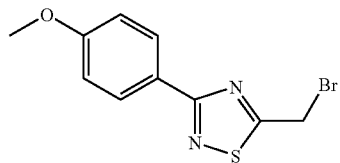

To a solution of [3-(4-methoxyphenyl)-[1,2,4]thiadiazol-5-yl]-methanol (0.07 g, 0.29 mmol) in toluene (10 ml) was added PBr₃ (0.041 ml, 0.43 mmol) and the resulting reaction mixture was refluxed at 120° C. for 15 min. After the completion of the reaction (TLC monitoring), the reaction mixture was cooled to 0° C., added water (50 ml) and extracted with ethyl acetate (3×50 ml). The combined organics was washed with saturated NaHCO₃ solution, dried over Na₂SO₄, filtered and concentrated under vacuum to get the desired product (0.048 g, 53%).

5-Bromomethyl-3-(4-trifluoromethoxyphenyl)-[1,2,4]thiadiazole: (V-c)

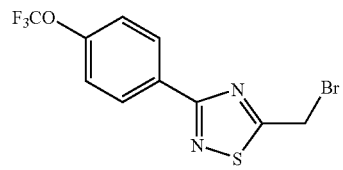 [SMILES: FC(F)(F)Oc1ccc(-c2nsc(CBr)n2)cc1]

To a solution of [3-(4-trifluoromethoxyphenyl)-[1,2,4]thiadiazol-5-yl]-methanol (0.10 g, 0.36 mmol) in toluene (5 ml) was added PBr₃ (0.050 ml, 0.54 mmol) and the resulting reaction mixture was refluxed at 120° C. for 15 min. After the completion of the reaction (TLC monitoring), the reaction mixture was cooled to 0° C., added water (50 ml) and extracted with ethyl acetate (3×50 ml). The combined organics was washed with saturated NaHCO₃ solution, dried over Na₂SO₄, filtered and concentrated under vacuum to get the desired product (0.11 g, 89%).

EXAMPLE 1

3-[3-(4-Chlorophenyl)-[1,2,4]thiadiazol-5-yl-methoxy]-2,6-difluorobenzamide (VI-a)

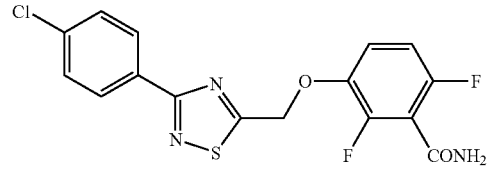 [SMILES: NC(=O)c1c(F)ccc(OCc2nc(-c3ccc(Cl)cc3)ns2)c1F]

To a solution of 5-bromomethyl-3-(4-chlorophenyl)-[1,2,4]thiadiazole (0.08 g, 0.30 mmol) in DMF (2 ml) was added 2,6-difluoro-3-hydroxybenzamide (0.046 g, 0.26 mmol) and potassium carbonate (0.14 g, 1.02 mmol). The reaction mixture was stirred at 25° C. for 12 h under nitrogen atmosphere. After the completion of the reaction (TLC monitoring), the reaction mixture was evaporated to dryness under vacuum, added 50 ml water and extracted with ethyl acetate (3×50 ml). The combined organic layer was dried over Na₂SO₄, filtered and concentrated under vacuum. The crude residue was purified over silica gel (100-200 M, 50% EtOAc-Hexane) to get the desired product (0.032 g, 76%).

¹H NMR (DMSO-d₆, 400 MHz): δ 5.82 (s, 2H), 7.13 (m, 1H), 7.44 (m, 1H), 7.63 (d, J=8.80 Hz, 2H), 7.90 (br s, 1H), 8.17 (br s, 1H) and 8.24 (d, J=8.80 Hz, 2H). MS ES+ (382.19).

HPLC (Xbridge C-18, 250×4.6 mm; 269 nm) Rt=17.14 min, 99.42%.

EXAMPLE 2

2,6-Difluoro-3-[3-(4-methoxyphenyl)-[1,2,4]thiadiazol-5-ylmethoxy]-benzamide: (VI-b)

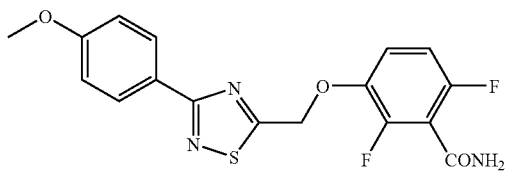 [SMILES: COc1ccc(-c2nsc(COc3ccc(F)c(C(N)=O)c3F)n2)cc1]

To a solution of 5-bromomethyl-3-(4-methoxyphenyl)-[1,2,4]thiadiazole (0.048 g, 0.15 mmol) in DMF (2 ml) was added 2,6-difluoro-3-hydroxybenzamide (0.027 g, 0.15 mmol) and potassium carbonate (0.76 g, 0.55 mmol). The reaction mixture was stirred at 25° C. for 12 h under nitrogen atmosphere. After the completion of the reaction (TLC monitoring), the reaction mixture was evaporated to dryness under vacuum, added 30 ml water and extracted with ethyl acetate (3×20 ml). The combined organic layer was dried over $Na_2SO_4$, filtered and concentrated under vacuum. The crude residue was purified over silica gel (100-200 M, 50% EtOAc-Hexane) to get the desired product (0.011 g, 30%).

$^1$H NMR (DMSO-$d_6$, 400 MHz): δ 3.83 (s, 3H), 5.80 (s, 2H), 7.10 (m, 3H), 7.50 (m, 1H), 7.90 (br s, 1H) and 8.18 (m, 3H). MS ES+ (378.17).

HPLC (Xbridge C-18, 250×4.6 mm; 278 nm) Rt=15.55 min, 99.83%.

EXAMPLE 3

2,6-Difluoro-3-[3-(4-trifluoromethoxyphenyl)-[1,2,4]thiadiazol-5-ylmethoxy]-benzamide: (VI-c)

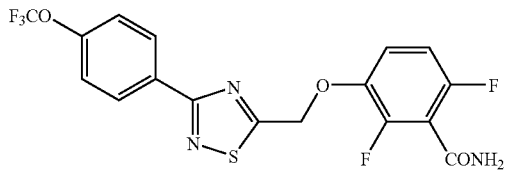 [SMILES: NC(=O)c1c(F)ccc(OCc2nc(-c3ccc(OC(F)(F)F)cc3)ns2)c1F]

To a solution of 5-bromomethyl-3-(4-trifluoromethoxyphenyl)-[1,2,4]thiadiazole (0.11 g, 0.32 mmol) in DMF (5 ml) was added 2,6-difluoro-3-hydroxybenzamide (0.056 g, 0.32 mmol) and potassium carbonate (0.16 g, 1.13 mmol). The reaction mixture was stirred at 25° C. for 12 h under nitrogen atmosphere. After the completion of the reaction (TLC monitoring), the reaction mixture was evaporated to dryness under vacuum, added 30 ml water and extracted with ethyl acetate (3×20 ml). The combined organic layer was dried over $Na_2SO_4$, filtered and concentrated under vacuum. The crude residue was purified over silica gel (100-200 M, 50% EtOAc-Hexane) to get the desired product (0.013 g, 9%).

$^1$H NMR (DMSO-$d_6$, 400 MHz): δ 5.83 (s, 2H), 7.15 (m, 1H), 7.44 (m, 1H), 7.57 (d, J=8.40 Hz, 2H), 7.90 (br s, 1H), 8.17 (br s, 1H) and 8.35 (d, J=8.40 Hz, 2H). MS ES+ (432.14).

HPLC (Xbridge C-18, 250×4.6 mm; 262 nm) Rt=17.31 min, 98.17%.

Scheme-2:

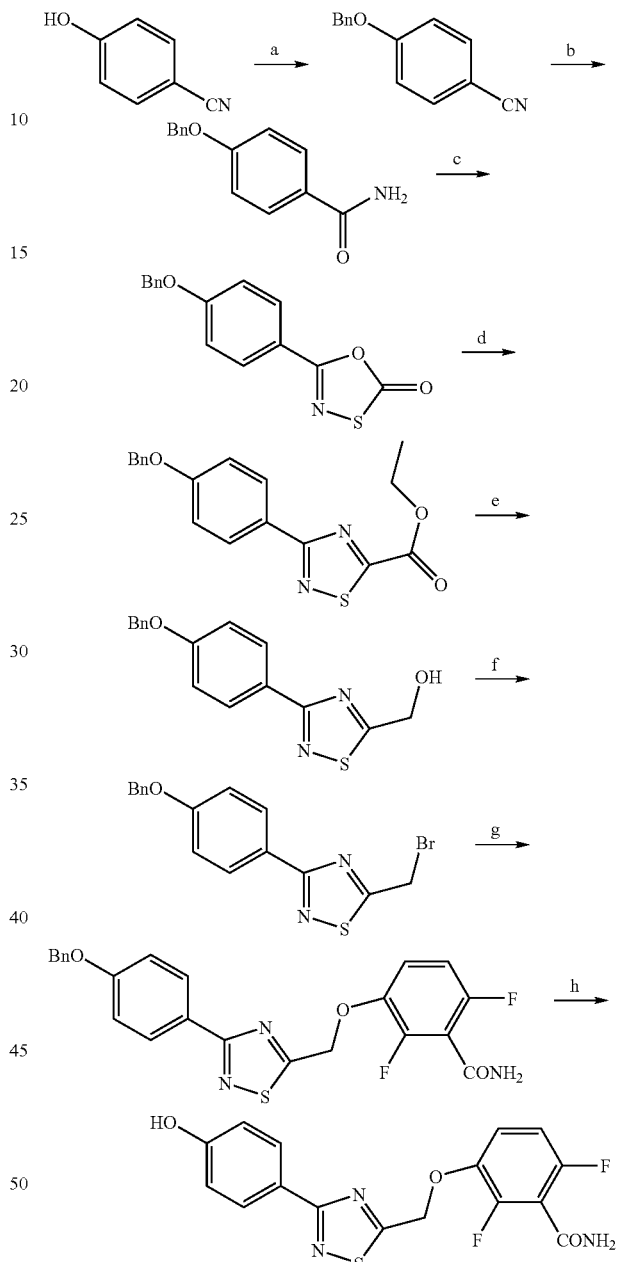

(a) Benzyl bromide, $K_2CO_3$, acetone; (b) KOH, tert-butanol, 78° C., 4 h; (c) Chlorocarbonylsulfenyl chloride, toluene, 90° C.; (d) Ethyl cyanoformate, 1,2 dichlorobenzene, 150° C.; (e) $NaBH_4$, EtOH; (f) $PBr_3$, toluene, 120° C.; (g) 2,6-Difluoro-3-hydroxybenzamide, $K_2CO_3$, DMF; (h) Methanesulfonic acid, DCM.

4-Benzyloxybenzonitrile

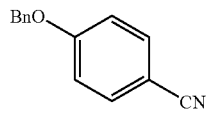

To an ice cold solution of 4-hydroxybenzonitrile (0.50 g, 4.19 mmol) in 10 ml of acetone was added potassium carbonate (0.76 g, 5.49 mmol) followed by benzyl bromide (0.32 ml, 2.73 mmol). The reaction mixture was stirred at 25° C. overnight under nitrogen atmosphere. After the completion of the reaction (TLC monitoring), the reaction mixture was evaporated to dryness under vacuum, added 50 ml water and extracted with ethyl acetate (3×40 ml). The combined organic layer was dried over $Na_2SO_4$, filtered and concentrated under vacuum. The crude residue was purified over silica gel (100-200 M, 10% EtOAc-Hexane) to get the desired product (0.75 g, 85%).

$^1$H NMR (CDCl$_3$, 400 MHz): δ 5.11 (s, 2H), 7.03 (d, J=8.80 Hz, 2H), 7.34-7.41 (m, 5H) and 7.59 (d, J=8.80 Hz, 2H), 4-Benzyloxybenzamide

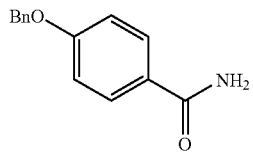 [SMILES: NC(=O)c1ccc(OCc2ccccc2)cc1]

To a solution of 4-benzyloxybenzonitrile (0.61 g, 2.91 mmol) in 15 ml of tert-butanol was added fine powder of KOH (1.22 g, 21.78 mmol) and the resulting reaction mixture was refluxed for 4 h at 78° C. After the completion of the reaction (TLC monitoring), added brine solution and extracted with ethyl acetate (3×50 ml). The combined organic layer was dried over $Na_2SO_4$, filtered and concentrated under vacuum, to get the product (0.67 g) that was used as such for the next step.

$^1$H NMR (DMSO-d$_6$, 400 MHz): δ 5.12 (s, 2H), 7.03 (d, J=8.80 Hz, 2H), 7.31 (br s, 1H), 7.32-7.46 (m, 5H) and 7.85 (m, 3H).

5-(4-Benzyloxyphenyl)-[1,3,4]oxathiazol-2-one

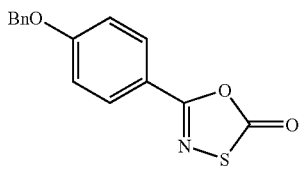 [SMILES: O=c1oc(-c2ccc(OCc3ccccc3)cc2)ns1]

To a solution of 4-benzyloxybenzamide (0.25 g, 1.10 mmol) in toluene (15 ml) was added chlorocarbonylsulfenyl chloride (0.18 ml, 2.20 mmol) and the resulting reaction mixture was refluxed at 90° C. overnight. After the completion of the reaction (TLC monitoring), the mixture was concentrated, added diethyl ether and washed twice with water, twice with 5% NaHCO$_3$, again with water, and was then dried (Na$_2$SO$_4$), concentrated under vacuum to give the product (crude yield 0.310 g, 98%) that was used as such for the next step.

3-(4-Benzyloxyphenyl)-[1,2,4]thiadiazole-5-carboxylic acid ethyl ester

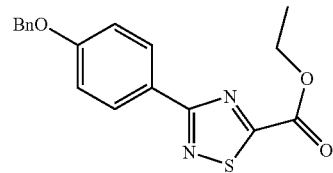 [SMILES: CCOC(=O)c1nc(-c2ccc(OCc3ccccc3)cc2)ns1]

To a solution of 5-(4-benzyloxyphenyl)-[1,3,4]oxathiazol-2-one (0.31 g, 1.08 mmol) in 1,2-dichlorobenzene (2 ml) was added ethyl cyanoformate (0.43 ml, 4.35 mmol). The resulting reaction mixture was refluxed overnight at 150° C. After the completion of the reaction (TLC monitoring), added ice-cold water and extracted with ethyl acetate (3×50 ml). The combined organic layer was dried over Na$_2$SO$_4$, filtered and concentrated under vacuum, to get the product (0.250 g, 65%). MS ES+ (341.12).

[3-(4-Benzyloxyphenyl)-[1,2,4]thiadiazol-5-yl]-methanol

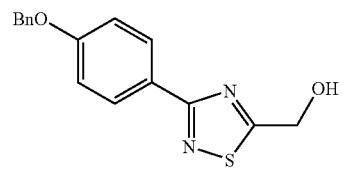 [SMILES: OCc1nc(-c2ccc(OCc3ccccc3)cc2)ns1]

To a solution of 3-(4-benzyloxyphenyl)-[1,2,4]thiadiazole-5-carboxylic acid ethyl ester (0.20 g, 0.59 mmol) in EtOH (20 ml) was added sodium borohydride (0.44 g, 1.17 mmol) portion wise and the resulting reaction mixture was stirred at room temperature for 2 h. After the completion of the reaction (TLC monitoring), the reaction mass was cooled to 0° C., quenched it with 5 ml of water and concentrated under vacuum. Added 75 ml water and extracted with ethyl acetate (3×30 ml). The combined organic layer was dried over Na$_2$SO$_4$, filtered and concentrated under vacuum. The crude residue was purified over silica gel (100-200 M, 30% EtOAc-Hexane) to get the desired product (0.052 g, 30%).

3-(4-Benzyloxyphenyl)-5-bromomethyl-[1,2,4]thiadiazole

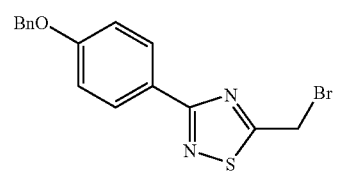 [SMILES: BrCc1nc(-c2ccc(OCc3ccccc3)cc2)ns1]

To a solution of [3-(4-benzyloxyphenyl)-[1,2,4]thiadiazol-5-yl]-methanol (0.052 g, 0.17 mmol) in toluene (5 ml) was added PBr₃ (0.027 ml, 0.26 mmol) and the resulting reaction mixture was refluxed at 120° C. for 15 min. After the completion of the reaction (TLC monitoring), the reaction mixture was cooled to 0° C., added water (50 ml) and extracted with ethyl acetate (3×50 ml). The combined organics was washed with saturated NaHCO₃ solution, dried over Na₂SO₄, filtered and concentrated under vacuum to get the desired product (0.043 g, 68%).

3-[3-(4-Benzyloxyphenyl)-[1,2,4]thiadiazol-5-yl-methoxy]-2,6-difluorobenzamide

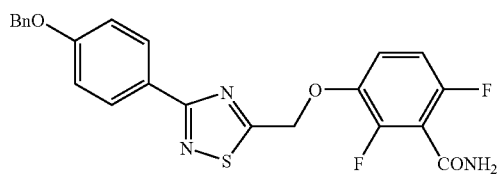 [SMILES: NC(=O)c1c(F)ccc(OCc2nc(-c3ccc(OCc4ccccc4)cc3)ns2)c1F]

To a solution of 3-(4-benzyloxyphenyl)-5-bromomethyl-[1,2,4]thiadiazole (0.04 g, 0.11 mmol) in DMF (2 ml) was added 2,6-difluoro-3-hydroxybenzamide (0.017 g, 0.10 mmol) and potassium carbonate (0.53 g, 0.39 mmol). The reaction mixture was stirred at 25° C. overnight under nitrogen atmosphere. After the completion of the reaction (TLC monitoring), the reaction mixture was evaporated to dryness under vacuum, added 20 ml water and extracted with ethyl acetate (3×20 ml). The combined organic layer was dried over Na₂SO₄, filtered and concentrated under vacuum. The crude residue was purified over silica gel (100-200 M, 40% EtOAc-Hexane) to get the desired product (0.025 g, 50%). MS ES+ (454.13).

EXAMPLE 4

2,6-Difluoro-3-[3-(4-hydroxyphenyl)-[1,2,4]thiadia-zol-5-ylmethoxy]-benzamide

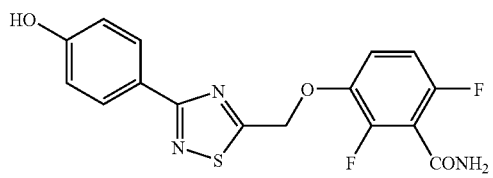 [SMILES: NC(=O)c1c(F)ccc(OCc2nc(-c3ccc(O)cc3)ns2)c1F]

To a solution of 3-[3-(4-benzyloxy-phenyl)-[1,2,4]thiadia-zol-5-ylmethoxy]-2,6-difluorobenzamide (0.020 g, 0.04 mmol) in DCM (5 ml) was added methanesulfonic acid (0.15 g, 1.50 mmol) drop wise. The resulting reaction mixture was stirred at room temperature for 1 h. After the completion of the reaction (TLC monitoring), the reaction mass was cooled to 0° C., quenched it with 5 ml of water and concentrated under vacuum. Added 25 ml water and extracted with ethyl acetate (3×20 ml). The combined organic layer was dried over Na₂SO₄, filtered and concentrated under vacuum. The crude residue was purified by ether and DCM washes to get the desired product (0.004 g, 25%).

¹H NMR (DMSO-d₆, 400 MHz): δ 5.79 (s, 2H), 6.90 (d, J=8.40 Hz, 2H), 7.14 (m, 1H), 7.42 (m, 1H), 7.90 (br s, 1H), 8.07 (d, J=8.40 Hz, 2H), 8.17 (br s, 1H) and 10.04 (br s, 1H). MS ES+ (364.16).

HPLC (Acquity BEH C-18, 100×2.1 mm) Rt=4.81 min, 96.74%.

Scheme-3:

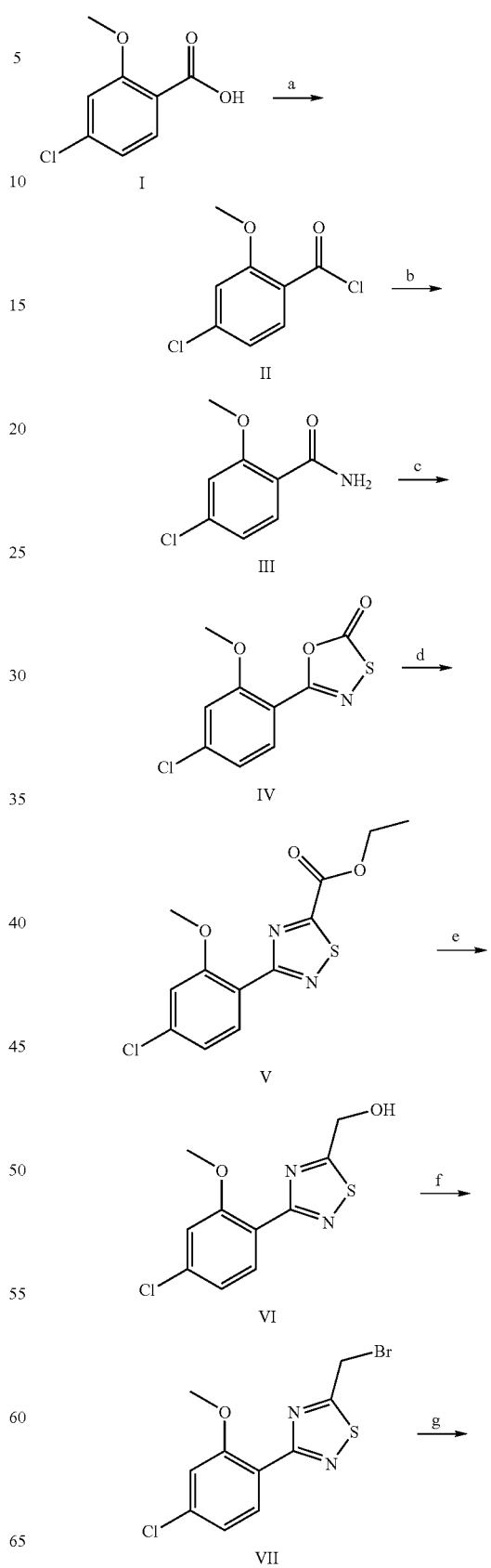

-continued

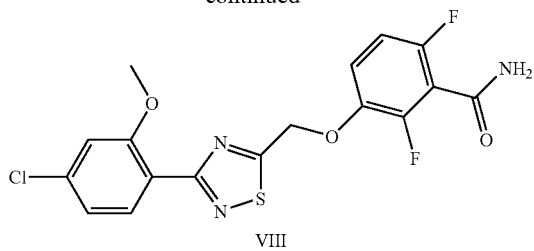

VIII (a) Thionyl chloride, toluene, 80° C., 1 h; (b) NH₃ (g), THF; (c) Chlorocarbonylsulfenyl chloride, toluene, 90° C., 2 h; (d) Ethyl cyanoformate, 1,2-dichlorobenzene, 150° C., 24 h; (e) NaBH₄, EtOH, 2 h; (f) PBr₃, toluene, 60° C., 2 h; (g) 2,6-difluoro-3-hydroxybenzamide, K₂CO₃, DMF.

4-Chloro-2-methoxybenzoyl chloride (II)

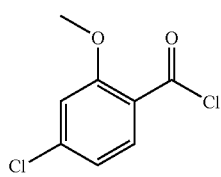

II

To a solution of 4-chloro-2-methoxybenzoic acid (1.0 g, 5.36 mmol) in toluene (10 ml) was added thionyl chloride (2.76 ml, 37.52 mmol) at room temperature under nitrogen atmosphere. The resulting reaction mixture was heated to 80° C. for 1 h. After the completion of the reaction (TLC monitoring), the solvent was evaporated under vacuum and was carried forward as such for the next step.

4-Chloro-2-methoxybenzamide (III)

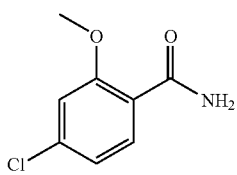

III

The crude 4-chloro-2-methoxybenzoyl chloride (obtained in the first step) was dissolved in dry THF (25 ml) and was purged with NH₃ (g) for 10 min and then left to stir at room temperature for 4 h. After the completion of the reaction (TLC monitoring), water was added and extracted with EtOAc (3×50 ml). The combined organics was dried over anhydrous Na₂SO₄, filtered and concentrated to get the desired product (0.82 g, 83% over 2 steps).

$^1$H NMR (DMSO-d₆, 400 MHz): δ 3.90 (s, 3H), 7.09 (dd, J=2.0 and 8.40 Hz respectively, 1H), 7.22 (d, J=2.0 Hz, 1H), 7.61 (br s, 2H) and 7.78 (d, J=8.40 Hz, 1H).

5-(4-Chloro-2-methoxyphenyl)-1,3,4-oxathiazol-2-one (IV)

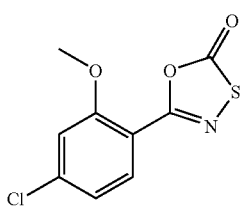

IV

To a solution of 4-chloro-2-methoxybenzamide (0.82 g, 4.42 mmol) in toluene (20 ml) was added chlorocarbonylsulfenyl chloride (0.73 ml, 8.84 mmol) under nitrogen atmosphere and the resulting reaction mixture was refluxed at 90° C. for 2 h. After the completion of the reaction (TLC monitoring) water was added followed by extraction with ether (3×50 ml). The combined organics was then sequentially washed with water, 10% NaHCO3 (aqueous solution) and finally again with water. The organic layer was then dried over anhydrous Na₂SO₄, filtered and concentrated to get desired product (1.03 g, 96% crude yield) that was carried forward as such without further purification. MS: 244.16 (M+H)⁺.

Ethyl 3-(4-chloro-2-methoxyphenyl)-1,2,4-thiadiazole-5-carboxylate (V)

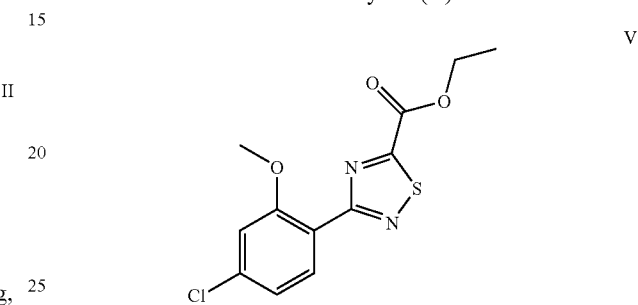

V

To a solution of 5-(4-chloro-2-methoxyphenyl)-1,3,4-oxathiazol-2-one (1.32 g, 5.42 mmol) in 1,2-dichlorobenzene (5 ml) was added ethyl cyanoformate (2.20 ml, 21.67 mmol). The resulting reaction mixture was refluxed for 24 h at 150° C. After the completion of the reaction (TLC monitoring), the reaction mass was as such (direct loading) purified through flash chromatography (100-200 M silica, 5% EtOAc-Hexane) to get the desired product (0.31 g, 19%). LCMS: 299.29 (M+H)⁺, 98.99%.

(3-(4-Chloro-2-methoxyphenyl)-1,2,4-thiadiazol-5-yl)methanol (VI)

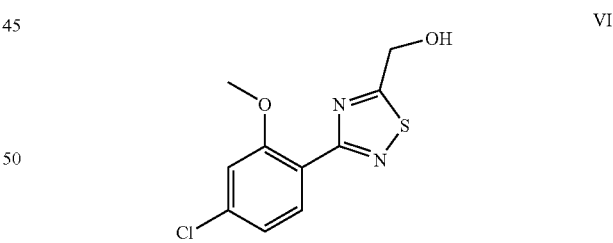

VI

To a solution of ethyl 3-(4-chloro-2-methoxyphenyl)-1,2,4-thiadiazole-5-carboxylate (0.31 g, 1.04 mmol) in EtOH (15 ml) was added sodium borohydride (0.098 g, 2.59 mmol) portion wise. The resulting reaction mixture was stirred at room temperature for 2 h. After the completion of the reaction (TLC monitoring), the reaction mass was cooled to 0° C., quenched it with 2 ml of water and concentrated under vacuum. Added water (50 ml) and extracted with ethyl acetate (3×50 ml). The combined organic layer was dried over Na₂SO₄, filtered and concentrated under vacuum to get the product (0.22 g, 92%) that was carried forward to the next step without further purification.

5-(Bromomethyl)-3-(4-chloro-2-methoxyphenyl)-1,2,4-thiadiazole (VII)

VII

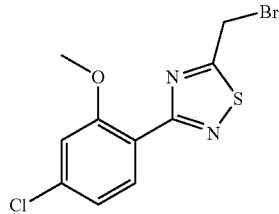

To a solution of (3-(4-chloro-2-methoxyphenyl)-1,2,4-thiadiazol-5-yl)methanol (0.08 g, 0.31 mmol) in toluene (4 ml) was added PBr$_3$ (49 µl, 0.47 mmol) and the resulting reaction mixture was heated at 60° C. for 2 h. After the completion of the reaction (TLC monitoring), the reaction mixture was cooled to 0° C., added water (50 ml) and extracted with ethyl acetate (3×50 ml). The combined organics was washed with saturated NaHCO$_3$ solution, dried over Na$_2$SO$_4$, filtered and concentrated under vacuum. The crude residue was purified over silica gel (100-200 M, 5% EtOAc-Hexane) to get the desired product (0.063 g, 64%). MS: 319 (M+H)$^+$.

EXAMPLE 5

3-((3-(4-chloro-2-methoxyphenyl)-1,2,4-thiadiazol-5-yl)methoxy)-2,6-difluorobenzamide (VIII)

VIII

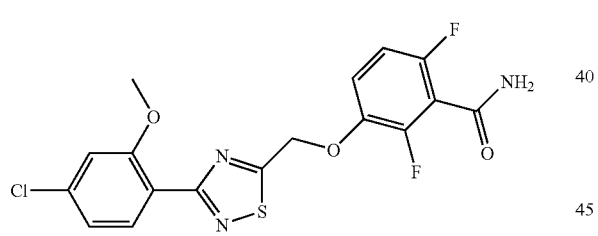

To a solution of 5-(bromomethyl)-3-(4-chloro-2-methoxyphenyl)-1,2,4-thiadiazole (0.06 g, 0.19 mmol) in DMF (4 ml) was added 2,6-difluoro-3-hydroxybenzamide (0.029 g, 0.17 mmol) and potassium carbonate (0.091 g, 0.66 mmol). The reaction mixture was stirred at room temperature for 90 min under nitrogen atmosphere. After the completion of the reaction (TLC monitoring), the reaction mixture was evaporated to dryness under vacuum, added 25 ml water and extracted with ethyl acetate (3×25 ml). The combined organic layer was dried over Na$_2$SO$_4$, filtered and concentrated under vacuum. The crude residue was purified over silica gel (100-200 M, 100% EtOAc) to get the desired product (0.02 g, 26%).

$^1$H NMR (DMSO-d$_6$, 400 MHz): δ 3.86 (s, 3H), 5.79 (s, 2H), 7.12-7.17 (m, 2H), 7.30 (d, J=2.0 Hz, 1H), 7.40-7.46 (m, 1H), 7.86 (d, J=8.0 Hz, 1H), 7.89 (br s, 1H) and 8.17 (br s, 1H).

MS: 412.11 (M+H)$^+$.

HPLC (Acquity BEH C-18, 100×2.1 mm; 214 nm) Rt=5.71 min, 95.48%.

Scheme-4:

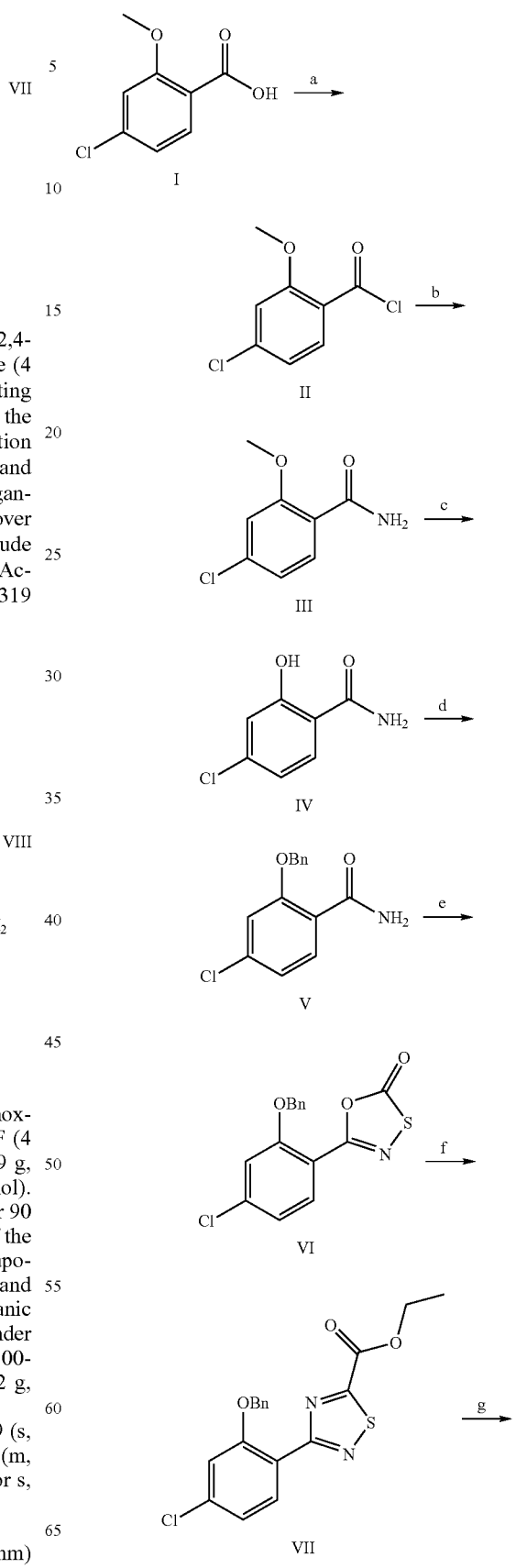

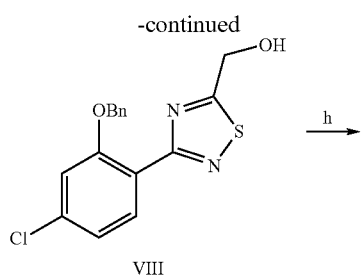

VIII

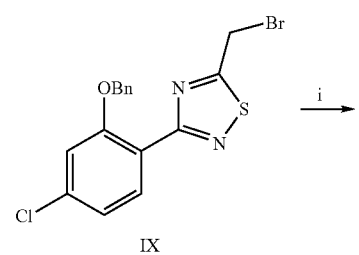

IX

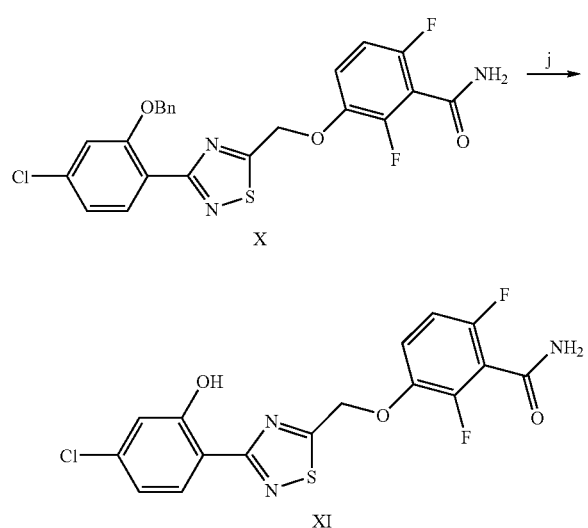

(a) Thionyl chloride, toluene, 80° C., 1 h; (b) NH₃ (g), THF; (c) BBr₃, DCM, -78° C., 2 h; (d) benzyl bromide, K₂CO₃, acetonitrile; (e) Chlorocarbonylsulfenyl chloride, toluene, 90° C., 2 h; (f) Ethyl cyanoformate, 1,2-dichlorobenzene, 150° C., 3 h; (g) NaBH₄, EtOH, 2 h; (h) PBr₃, toluene, 100° C., 15 min; (i) 2,6-difluoro-3-hydroxybenzamide, K₂CO₃, DMF; (j) Methane sulfonic acid, DCM.

Preparation of intermediates I-II as per Scheme-3.

4-Chloro-2-hydroxybenzamide (IV)

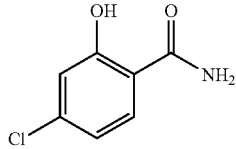

IV

A solution of 4-chloro-2-methoxybenzamide (0.74 g, 3.99 mmol) in dichloromethane (50 ml) was cooled to −78° C. followed by addition of BBr₃ (1.15 ml, 11.96 mmol) under nitrogen atmosphere. The reaction mixture was allowed to stir at room temperature for 2 h. After the completion of reaction (TLC monitoring), the solution was cooled to 0° C. and quenched with water. The resulting solution was basified by aqueous NaHCO₃ and extracted with EtOAc (3×100 ml). The combined organics was dried over anhydrous Na₂SO₄, filtered and concentrated to get the desired product (0.608 g, 89%). MS: 172.33 (M+H)⁺.

2-(Benzyloxy)-4-chlorobenzamide (V)

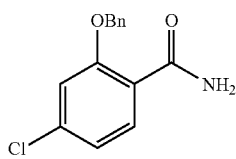

V

To a solution of 4-chloro-2-hydroxybenzamide (0.608 g, 3.54 mmol) in acetonitrile (50 ml) was added dried K₂CO₃ (1.71 g, 12.40 mmol) followed by benzyl bromide (0.63 ml, 5.32 mmol) and the resulting reaction mixture was refluxed at 80° C. for 16 h. After the completion of the reaction (TLC monitoring), water was added followed by extraction with EtOAc (3×100 ml). The combined organics was dried over anhydrous Na₂SO₄, filtered and concentrated. The residue was washed repeatedly with hexane to get rid of the excess of benzyl bromide resulting the desired product (0.75 g, 81%).

¹H NMR (DMSO-d₆, 400 MHz): δ 5.28 (s, 2H), 7.11 (dd, J=2.0 and 8.40 Hz respectively, 1H), 7.32 (d, J=1.60 Hz, 1H), 7.37 (m, 1H), 7.39-7.45 (m, 2H), 7.49-7.51 (m, 2H), 7.57 (br s, 1H), 7.62 (br s, 1H) and 7.76 (d, J=8.40 Hz, 1H). MS: 262.24 (M+H)⁺.

5-(2-(Benzyloxy)-4-chlorophenyl)-1,3,4-oxathiazol-2-one (VI)

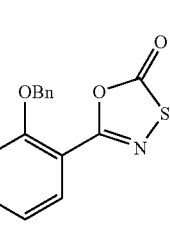

VI

To a solution of 2-(benzyloxy)-4-chlorobenzamide (0.103 g, 0.38 mmol) in toluene (5 ml) was added chlorocarbonylsulfenyl chloride (63 μL, 0.76 mmol) under nitrogen atmosphere and the resulting reaction mixture was refluxed at 90° C. for 2 h. After the completion of the reaction (TLC monitoring) water was added followed by extraction with ether (3×25 ml). The combined organics was then sequentially washed with water, 10% NaHCO₃ (aqueous solution) and finally again with water. The organic layer was then dried over anhydrous Na₂SO₄, filtered and concentrated to get desired product (0.12 g, 94%) that was carried forward as such without further purification. MS: 320.21 (M+H)+.

Ethyl 3-(2-(benzyloxy)-4-chlorophenyl)-1,2,4-thiadiazole-5-carboxylate (VII)

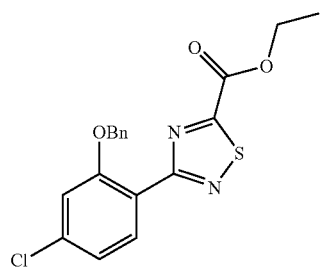

VII

To a solution of 5-(2-(benzyloxy)-4-chlorophenyl)-1,3,4-oxathiazol-2-one (0.15 g, 0.47 mmol) in 1,2-dichlorobenzene (1 ml) was added ethyl cyanoformate (185 µL, 1.88 mmol). The resulting reaction mixture was refluxed for 3 h at 150° C. After the completion of the reaction (TLC monitoring), the reaction mass was as such (direct loading) purified through flash chromatography (100-200 M silica, 2% EtOAc-Hexane) to get the desired product (0.02 g, 12%). MS: 375.18 (M+H)+.

(3-(2-(Benzyloxy)-4-chlorophenyl)-1,2,4-thiadiazol-5-yl) methanol (VIII)

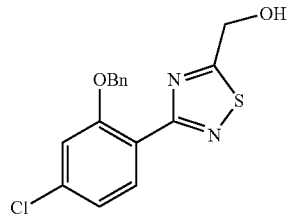

VIII

To a solution of ethyl 3-(2-(benzyloxy)-4-chlorophenyl)-1,2,4-thiadiazole-5-carboxylate (0.45 g, 1.20 mmol) in EtOH (25 ml) was added sodium borohydride (0.113 g, 3.0 mmol) portion wise. The resulting reaction mixture was stirred at room temperature for 2 h. After the completion of the reaction (TLC monitoring), the reaction mass was cooled to 0° C., quenched it with 2 ml of water and concentrated under vacuum. Added water (50 ml) and extracted with ethyl acetate (3×50 ml). The combined organic layer was dried over Na2SO4, filtered and concentrated under vacuum to get the desired product (0.35 g, 88%) that was carried forward to the next step without further purification.

3-(2-(Benzyloxy)-4-chlorophenyl)-5-(bromomethyl)-1,2,4-thiadiazole (IX)

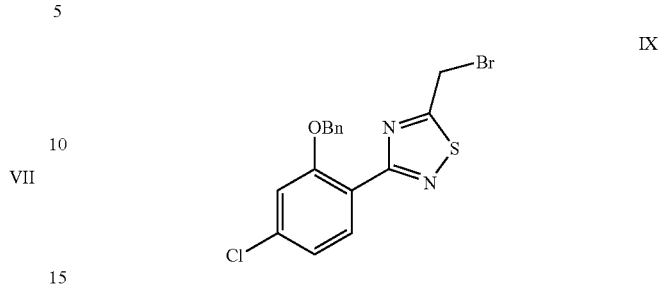

IX

To a solution of (3-(2-(benzyloxy)-4-chlorophenyl)-1,2,4-thiadiazol-5-yl) methanol (0.35 g, 1.05 mmol) in toluene (10 ml) was added PBr3 (0.16 ml, 1.58 mmol) and the resulting reaction mixture was heated at 100° C. for 15 min. After the completion of the reaction (TLC monitoring), the reaction mixture was cooled to 0° C., added water (50 ml) and extracted with ethyl acetate (3×50 ml). The combined organics was washed with saturated NaHCO3 solution, dried over Na2SO4, filtered and concentrated under vacuum to get the desired product (0.33 g, 79% crude yield), that was carried forward as such for the next step. MS: 395.05 (M+H)+.

EXAMPLE 6

3-((3-(2-(Benzyloxy)-4-chlorophenyl)-1,2,4-thiadiazol-5-yl)methoxy)-2,6-difluorobenzamide (X)

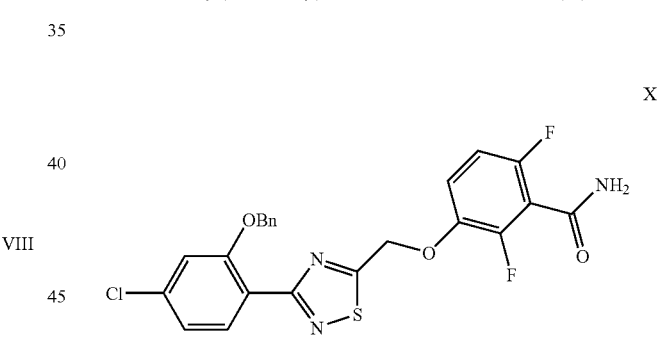

X

To a solution of 3-(2-(benzyloxy)-4-chlorophenyl)-5-(bromomethyl)-1,2,4-thiadiazole (0.33 g, 0.83 mmol) in DMF (10 ml) was added 2,6-difluoro-3-hydroxybenzamide (0.13 g, 0.75 mmol) and potassium carbonate (0.403 g, 2.92 mmol). The reaction mixture was stirred at room temperature for 16 h under nitrogen atmosphere. After the completion of the reaction (TLC monitoring), the reaction mixture was evaporated to dryness under vacuum, added 25 ml water and extracted with ethyl acetate (3×25 ml). The combined organic layer was dried over Na2SO4, filtered and concentrated under vacuum. The crude residue was purified over silica gel (100-200 M, 40% EtOAc-Hexane) to get the desired product (0.123 g, 30%).

$^1$H NMR (DMSO-$d_6$, 400 MHz): δ 5.30 (s, 2H), 5.82 (s, 2H), 7.10-7.19 (m, 2H), 7.29 (t, J=7.20 Hz, 1H), 7.36-7.40 (m, 3H), 7.42-7.46 (m, 1H), 7.53 (d, J=7.20 Hz, 2H), 7.92 (d, J=8.40 Hz, 2H) and 8.19 (br s, 1H). MS: 488.13 (M+H)+.

HPLC (Acquity BEH C-18, 100×2.1 mm; 214 nm) Rt=6.51 min, 85.44%.

EXAMPLE 7

3-((3-(4-chloro-2-hydroxyphenyl)-1,2,4-thiadiazol-5-yl)methoxy)-2,6-difluorobenzamide (XI)

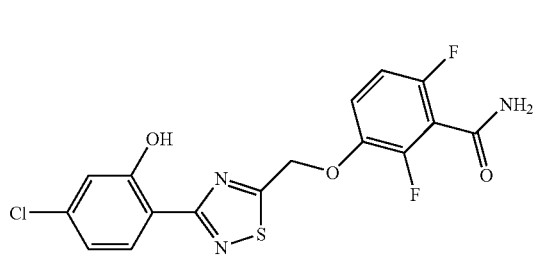 [SMILES: NC(=O)c1c(F)ccc(OCc2nc(-c3ccc(Cl)cc3OCc3ccccc3)ns2)c1F]

To a solution of 3-((3-(2-(benzyloxy)-4-chlorophenyl)-1,2,4-thiadiazol-5-yl)methoxy)-2,6-difluorobenzamide (0.05 g, 0.10 mmol) in dichloromethane (5 ml) was added methanesulfonic acid (0.50 ml, excess) at room temperature under nitrogen atmosphere and allowed to stir at same temperature for 90 min. After the completion of the reaction (TLC monitoring), the solution was cooled to 0° C. and basified with saturated NaHCO$_3$ solution (aqueous) followed by extraction with EtOAc (3×25 ml). The combined organics was dried over anhydrous Na$_2$SO$_4$, filtered and concentrated. The residue was washed with ether to get the desired product (0.012 g, 30%).

$^1$H NMR (DMSO-d$_6$, 400 MHz): δ 5.87 (s, 2H), 7.10-7.16 (m, 3H), 7.42-7.48 (m, 1H), 7.92 (br s, 1H), 8.14 (d, J=8.40 Hz, 1H), 8.19 (br s, 1H) and 11.05 (br s, 1H). MS: 398.01 (M+H)$^+$.

HPLC (Acquity BEH C-18, 100×2.1 mm; 254 nm) Rt=6.31 min, 91.69%.

Minimum Inhibitory Concentration (MIC) Testing

Compounds of this invention were tested for antimicrobial activity by susceptibility testing in liquid or on solid media. MICs for compounds against each strain were determined by the broth microdilution or agar dilution method according to the guidelines of the Clinical Laboratories and Standards Institute, formerly the National Committee for Clinical Laboratory Standards (Clinical Laboratories and Standards Institute. *Methods for Dilution Antimicrobial Susceptibility Tests for Bacteria That Grow Aerobically, Approved Standard—Seventh Edition*. Document M7-A7. CLSI, Wayne, Pa., 2006; Clinical Laboratories and Standards Institute.

Compounds of the current invention were found to have antimicrobial activity in the MIC assay described above.

Results

Table 1 shows the Minimal Inhibitory Concentration (MIC) of the Examples against the pathogenic organism *Staphylococcus aureus* ATCC29213. Activities were scored as 'A' if the MIC was ≦1.125 micrograms/ml, 'B' if the MIC was 0.25 to 4 micrograms/ml and 'C' if the MIC was greater than 4 micrograms/ml.

TABLE 1

*Staphylococcus aureus* MICs

| Example | Activity |
|---------|----------|
| 1 | A |
| 2 | A |
| 3 | A |
| 4 | B |
| 5 | B |
| 6 | B |
| 7 | A |
| — | — |

The invention claimed is:

1. A compound which is a substituted thiadiazolylmethoxybenzamide or thiadiazolylmethoxypyridylamide of formula (IA), or a salt thereof:

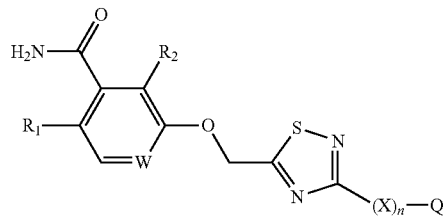

(IA)

wherein

W is =CH— or =N—;

R$_1$ and R$_2$ are independently selected from hydrogen, fluoro and chloro, provided that R$_1$ and R$_2$ are not each hydrogen when W is =CH—;

n is 0 or 1;

X is —O—, —S—, or —CH$_2$—; and

Q is (i) a phenyl radical, a naphthyl radical, a monocyclic carbocyclic or heteroaryl radical having 3 to 6 ring atoms, or a bicyclic heteroaryl radical having 5 to 10 ring atoms, any of which radicals being optionally substituted; or (ii) an optionally substituted C$_1$-C$_6$ alkyl, C$_2$-C$_6$ alkenyl, or C$_2$-C$_6$ alkynyl radical, which may optionally be interrupted by —O—, —S—, —S(O)—, —S(O$_2$)—, —NH—, —N(CH$_3$)—, —N(CH$_2$CH$_3$)—, —C(=O)—, or —C(=O)—O—.

2. A compound as claimed in claim 1 wherein W is =CH—.

3. A compound as claimed in claim 2 wherein R$_1$ and R$_2$ are independently fluoro or chloro, or one of R$_1$ and R$_2$ is hydrogen while the other is fluoro or chloro.

4. A compound as claimed in claim 1 wherein Q is optionally substituted phenyl.

5. A compound as claimed in claim 1 wherein Q is optionally substituted pyridin-2-yl, or pyridin-3-yl.

6. A compound as claimed in claim 4 wherein any optional substituents in Q are selected from methyl, —OCH$_3$, —OCH$_2$CH$_3$, —CF$_3$, —OCF$_3$, ethyl, cyclopropyl, oxo, hydroxyl, —F, —Cl, —Br, cyano, acetyl, amino, methylamino, dimethylamino, acetylamino, carbamate, —CONH$_2$, nitro, —COOH and —CH$_2$OH.

7. A compound as claimed in claim 4 wherein n is 0.

8. A compound selected from the group consisting of:
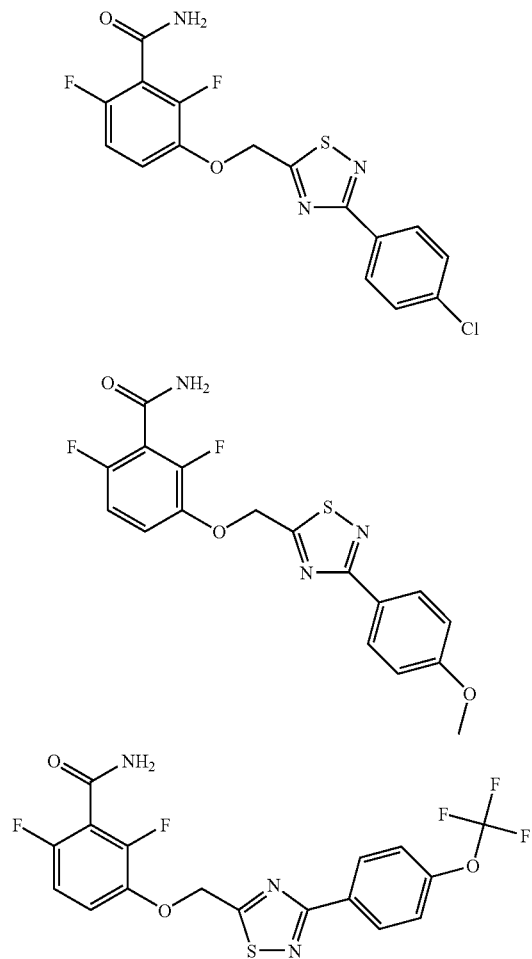
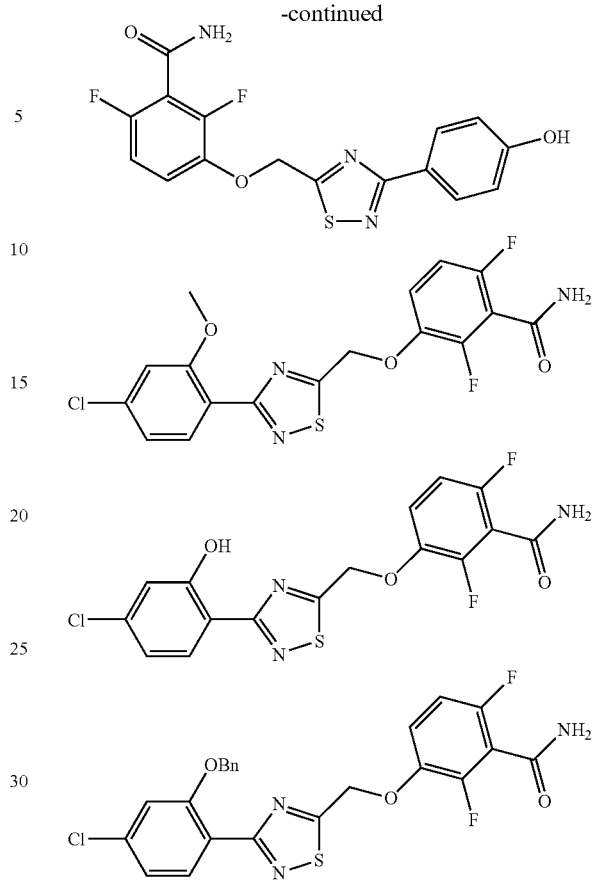
and salts thereof.
9. A pharmaceutical composition comprising a compound as claimed in claim 1, together with a pharmaceutically acceptable carrier.
* * * * *

UNITED STATES PATENT AND TRADEMARK OFFICE
CERTIFICATE OF CORRECTION

PATENT NO. : 8,492,414 B2  
APPLICATION NO. : 12/678767  
DATED : July 23, 2013  
INVENTOR(S) : David John Haydon et al.

Page 1 of 1

It is certified that error appears in the above-identified patent and that said Letters Patent is hereby corrected as shown below:

On the title page (item 57) in the Abstract:

Please delete

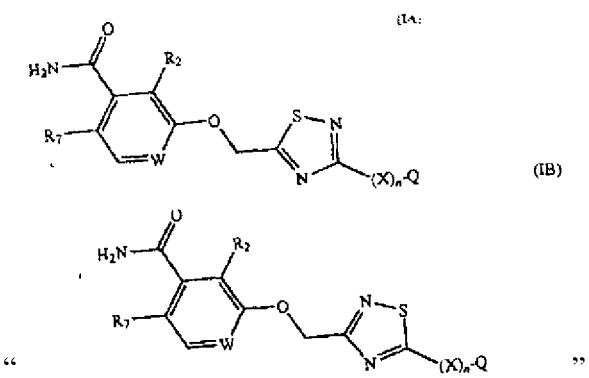

Please insert:

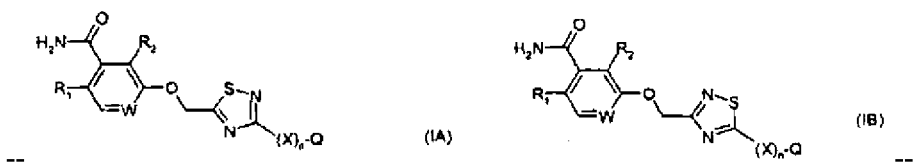

Signed and Sealed this  
Thirtieth Day of September, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,492,414 B2  Page 1 of 1
APPLICATION NO. : 12/678767
DATED : July 23, 2013
INVENTOR(S) : Haydon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 534 days.

Signed and Sealed this

Eighth Day of September, 2015

Michelle K. Lee
*Director of the United States Patent and Trademark Office*